(12) United States Patent
Poli

(10) Patent No.: US 10,912,785 B2
(45) Date of Patent: Feb. 9, 2021

(54) COMPOSITION AND MEDICAL DEVICE COMPRISING ACETYLSALICYLIC ACID FOR THE TREATMENT OF HUMAN PAPILLOMA VIRUS SKIN INFECTIONS

(71) Applicant: Poli MD S.R.L., Rome (IT)

(72) Inventor: Elena Poli, Rome (IT)

(73) Assignee: Poli MD S.R.L., Rome (IT)

( * ) Notice: Subject to any disclaimer, the term of this patent is extended or adjusted under 35 U.S.C. 154(b) by 122 days.

(21) Appl. No.: 15/756,724

(22) PCT Filed: Sep. 5, 2016

(86) PCT No.: PCT/IB2016/055300
§ 371 (c)(1),
(2) Date: Mar. 1, 2018

(87) PCT Pub. No.: WO2017/037684
PCT Pub. Date: Mar. 9, 2017

(65) Prior Publication Data
US 2018/0243321 A1 Aug. 30, 2018

(30) Foreign Application Priority Data

Sep. 4, 2015 (IT) .................. 102015000048609
May 13, 2016 (IT) .................. 102016000049308

(51) Int. Cl.
| *A61K 31/616* | (2006.01) |
|---|---|
| *A61K 9/70* | (2006.01) |
| *A61K 45/06* | (2006.01) |
| *A61K 47/69* | (2017.01) |
| *C08B 37/16* | (2006.01) |
| *C08L 1/26* | (2006.01) |
| *C08L 5/04* | (2006.01) |
| *C08L 5/00* | (2006.01) |
| *C08L 5/12* | (2006.01) |
| *A61K 9/00* | (2006.01) |
| *A61K 9/16* | (2006.01) |
| *A61K 47/38* | (2006.01) |
| *A61K 47/36* | (2006.01) |

(52) U.S. Cl.
CPC .......... *A61K 31/616* (2013.01); *A61K 9/7046* (2013.01); *A61K 9/7084* (2013.01); *A61K 45/06* (2013.01); *A61K 47/6951* (2017.08); *C08B 37/0015* (2013.01); *C08L 1/26* (2013.01); *C08L 5/00* (2013.01); *C08L 5/04* (2013.01); *C08L 5/12* (2013.01); *A61K 9/0014* (2013.01); *A61K 9/1617* (2013.01); *A61K 9/1652* (2013.01); *A61K 47/36* (2013.01); *A61K 47/38* (2013.01)

(58) Field of Classification Search
None
See application file for complete search history.

(56) References Cited

U.S. PATENT DOCUMENTS

| 5,914,322 | A | * | 6/1999 | Falk | ...................... | A61K 9/0014 |
|---|---|---|---|---|---|---|
| | | | | | | 514/54 |
| 2003/0072814 | A1 | * | 4/2003 | Maibach | .............. | A61K 8/0208 |
| | | | | | | 424/722 |
| 2008/0312196 | A1 | * | 12/2008 | Cohen | ................... | A61K 9/0014 |
| | | | | | | 514/163 |

* cited by examiner

*Primary Examiner* — Dennis J Parad
(74) *Attorney, Agent, or Firm* — MacMillan, Sobanski & Todd, LLC

(57) ABSTRACT

A medical device for the treatment of papilloma virus (HPV) skin infections is the object of this invention, in particular for the treatment of warts and related pathologies. In particular, this invention relates to acetylsalicylic acid for use in the topical treatment, of HPV skin infections in particular benign infections and more in particular warts. Acetylsalicylic acid may be administered by plaster or patch, both in a solid state, such as a tablet, powder or granulate, and by a hydrophilic or hydrophobic gel.

6 Claims, 1 Drawing Sheet

COMPOSITION AND MEDICAL DEVICE COMPRISING ACETYLSALICYLIC ACID FOR THE TREATMENT OF HUMAN PAPILLOMA VIRUS SKIN INFECTIONS

This is a national stage application filed under 35 U.S.C. § 371 of international application PCT/IB2016/055300, filed under the authority of the Patent Cooperation Treaty on Sep. 5, 2016, published; which claims the benefit of Italy Patent Application No. 102015000048609, filed on Sep. 4, 2015, and Italy Patent Application No. 102016000049308, filed on May 13, 2016. The entire disclosures of all the aforementioned applications are expressly incorporated herein by reference for all purposes.

FIELD OF THE INVENTION

A medical device for the treatment of papilloma virus (HPV) skin infections is the object of this invention, in particular for the treatment of warts and related pathologies.

BACKGROUND ART

Human papilloma viruses (HPV) are small DNA viruses of the papovavirus family. Though not being capsulated, HPV are very resistant viruses, with a diameter of about nm. Their genome consists of a double chain of circular DNA containing about 8000 nucleotide base pairs, associated with histones to form structures similar to small chromosomal bodies.

According to their trophism, HPVs may be classified as cutaneous and mucousal. The cutaneous types are differentiated into those commonly spread among the population (HPV 1, 2 and 4) and those associated with epidermodysplasia verruciformis, the most important of which are HPV 5 and HPV 8 due to the strong tendency in relation to malignant transformation. The mucousal types are generally divided into high and low risk types. The low risk types (HPV 6 and 11) are almost always absent in invasive squamocellular carcinomas, whereas the high-risk types are always present (HPV 16 and 18).

The benign HPV skin infections are generally classified as warts, papillomata and condylomata. Papillomata affect the oral cavity, whereas condylomata afflict the genital organs of both men and women.

A wart is a cutaneous formation induced by the human papillomavirus (HPV) and is a benign manifestation composed of a nucleus of interior tissue fed by blood vessels and covered by layers of epithelial tissue. The virus penetrates into the epidermis, infecting it.

The appearance of the wart changes depending on the location of the viral strain that caused it. Warts are divided into:
1. Common warts: the skin lesions provoked by Papilloma virus generally exhibit an irregular shape and often (but not always) develop in asymptomatically.
2. Plantar warts: typical of the sole of the foot, these wart lesions caused by HPV are easily transmitted in pools and in gyms.
3. Flat warts: wart lesions slightly in relief; the Papilloma virus, infecting hands, feet, the face and the legs may cause these skin lesions, that tend to disappear in a short while.

Common warts exhibit a typically rough surface, often crispate and of an unaesthetic appearance, and normally appear on the hands, on the elbows and on the knees.

Warts are a rather common problem: it is estimated that they afflict about 10% of the global population, with a tendency to increase. The population bracket hardest hit is school-age children, youths and young adults. The peak is reached in the age bracket between 10 and 15 years old.

Warts are often asymptomatic and tend to disappear even though, if not treated, healing times are very long, even lasting several years. Given the unaesthetic appearance of these skin manifestations, the afflicted subjects often resort to treatments to eliminate them.

The treatments currently used include:
surgical excision: consisting in the total excision of the skin infected. Although this method is effective, it is very invasive and in any case does not eliminate the problem of relapse of the wart;
cryotherapy: this consists in freezing the area concerned with liquid nitrogen;
keratolytic preparations: these accelerate the wart's aging cycle, causing it to rise to the surface and allowing its spontaneous detachment;
intralesional injections: injections of interferon inside the wart itself, so as to induce apoptosis of the cells infected by the virus;
Lasertherapy: consists in burning the wart by laser;
application of vitamin E: vitamin E, in oily preparations also used as anti-irritation skin cream, applied locally leads to the elimination of the wart, probably improving cicatrization capacity.

These treatments are for the most part invasive and have a probability of success below or equal to 70%.

There is therefore a need of a treatment for HPV skin infections, in particular the benign skin infections such as warts and similar manifestations, that is effective and slightly invasive or not at all.

Acetylsalicylic acid (ASA) belongs to the class of non-steroidal anti-inflammatory drugs (NSAID). ASA is a derivative of salicylic acid, differing from it due to the presence of an acetyl group in position 2, responsible for the molecule's anti-inflammatory activity. ASA acts inhibiting the synthesis of prostaglandin via acetylation of serine in the active site of the cyclooxygenase enzyme (COX). At low doses (75-81 mg/day), ASA's action of is selective at the platelet level, where it irreversibly inhibits serin 530 of COX1, producing an antithrombotic effect. At higher doses (650-4000 mg/day), ASA inhibits COX1 and COX2, blocking prostaglandin synthesis and having an antipyretic and analgesic effect. Other action mechanisms of the molecule have been studied or proposed to explain its numerous pharmacological properties, but little is known with relation to a possible antiviral activity of ASA. ASA, like other COX2 inhibitors, could be, capable of acting on cytomegalovirus (CMV), a pathogenic agent of the Herpes virus family. Scientific evidences have suggested that ASA may block the influenza virus.

SUMMARY OF THE INVENTION

It has now been discovered that acetylsalicylic acid for use in the topical treatment of HPV skin infections is effective in the treatment of HPV skin infections, in particular benign infections such as warts and similar manifestations, eliminating, in a few hours, the stratum corneum that characterizes such manifestations.

Without being tied to a particular theory, although no scientific evidence exists with relation to ASA's activity against the HPV, its capacity to interfere with the cellular pathway chosen by the virus to propagate in the host could explain its effectiveness in treating said skin infections.

Another possible mechanism could be attributable to a keratolytic effect exerted by ASA directly on the cutaneous manifestation, with the separation of the epidermal layer from the dermis through the accelerated loss of cells. ASA inhibits the synthesis of COX1 and influences the prostaglandin pathway, weakening the intercellular bonds of the corneocytes, that interrupt the adhesion thereof in the underlying stratum corneum, causing the upper stratum to separate from the newly formed lower stratum.

More likely, given the high treatment effectiveness observed, ASA acts through the concurrence of various mechanisms operating synergically.

One object of this invention therefore is the acetylsalicylic acid for use in the treatment of HPV skin infections in particular benign infections such as warts, papillomata and condylomata, according to the attached claims.

An additional object of the invention is a medical device for topical application, preferably via controlled release, comprising acetylsalicylic acid in the solid form or embedded in a polymer matrix of various natures, according to the claims.

Further features and advantages of the process according to the invention will result from the following description of preferred but not exclusive examples of embodiments.

DETAILED DESCRIPTION OF THE INVENTION

Figure 1:
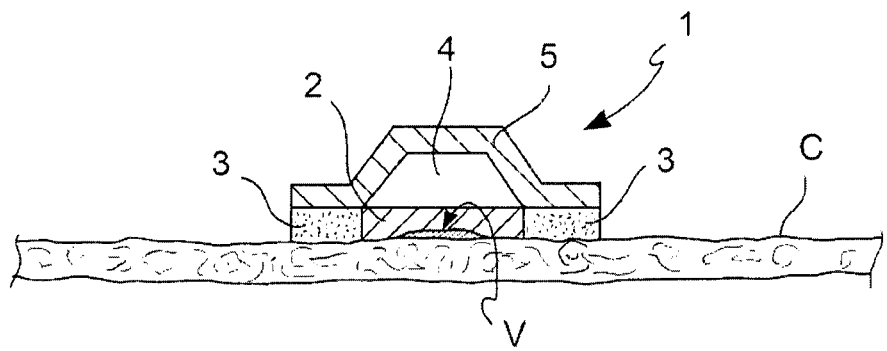
FIG. 1 depicts a schematic cross-section view of a first embodiment of the medical device according to the invention.

This invention relates to acetylsalicylic acid for use in the treatment of HPV skin infections in particular of benign skin infections such as warts, whether common or plantar or flat, papillomata, condylomata, etc.

In certain embodiments, the skin infections treated with acid acetylsalicylic according to the invention are the so-called genital warts, more often known as condylomata acuminato, that appear as excrescences or protuberances on the skin. Said condylomata are the expression of an HPV genital infection transmitted through sexual routes, even though the possibility of infection by other non-sexual routes cannot be ruled out.

In the male, the condylomata occur, preferentially, at the gland level, urinary meatus, frenulum, penis, and sulcus of the preputial gland; in women, instead, the areas most affected are the vulva, the neck of the uterus and the vagina.

The condylomata may be in relief or flat, large or small; sometimes they may be grouped together and take on a form that is similar to a polyp or an cauliflower. In some cases the warts have the same color as the skin and so small and flat that they can pass unobserved. Frequently, condylomata are asymptomatic, even though certain variations generate a burning sensation, itching and local irritation.

Acetylsalicylic acid (ASA) in accordance with this invention is used for topical administration, in solid state or embedded in a polymer matrix.

In preferred embodiments, the dosage of ASA is comprised between 0.3 and 5 g/day, or between 0.3 and 4 or between 0.3 and 1.2 g/day, preferably between 0.5 and 1 g/day.

In general, ASA will be contained in a patch or plaster comprising a layer or adhesive material facing the skin to be treated and an impermeable layer facing outward.

The impermeable layer is preferably selected from:
polyethylene terephthalate film (PET)
polyethylene film
polyurethane film
polyamide film
ethylene vinyl alcohol co-polymer (EVA) film
laminates comprising two or more layers of film selected from those listed above.

In the case of laminates, they may be manufactured by bonding or by coextrusion.

These films are commercial and well-known to the experts.

The layer or adhesive material may be in the form of strips, arranged along opposing ends of the plaster, for example, or along its perimeter, in a continuous or discontinuous line. In other embodiments, the layer or adhesive material takes the form of square or round pads, or of other shapes, arranged in discrete areas of the plaster face facing the skin to be treated.

The adhesive used for the purpose of this invention is an easily removable adhesive. In certain embodiments, a "hot melt" type glue comprising a thermoplastic polymer and containing zinc oxide, preferably in weighted amounts comprised between 5% and 35%, more preferably between 10% and 20%, are used.

In certain embodiments, the thermoplastic polymer is selected from: acrylic polymers, butyl rubber, ethylene vinyl acetate (EVA) polymers, natural rubber, nitrile polymers, silicon rubbers, styrene co-polymers, preferably styrene butylene co-polymer (SBC, SBS), styrene-ethylene-butylene-styrene co-polymer (SEBS), styrene-ethylene-propylene co-polymer (SEP) or styrene-isoprene-styrene (SIS) copolymer, or vinyl polymers.

In the preferred embodiment, the thermoplastic polymer is added with agents that favor adhesion. In the preferred embodiment, such agents are selected from: terpenes and modified terpenes, cycloaliphatic resins, aromatic resins, rosin, hydrogenated hydrocarbon resins, terpene phenol resins and silicone resins.

In certain embodiments, ASA is used in the form of a tablet applied on the cutaneous manifestation to be treated by means of a plaster or patch as set forth above.

In other embodiments, ASA is contained in a polymer matrix, e.g. in the form of a hydrophilic or hydrophobic gel or in the form of a tablet.

Hydrophilic Gels:
The gelling liquid phase is water.
In preferred embodiments, the gelling substances are selected from:
polyacrylic acid and salts thereof, e.g. Carbopol-934,
carboxymethyl cellulose,
hydroxypropyl cellulose,
methylcellulose 400 and 4000 cPs,
hydroxyethylcellulose,
hydroxypropylmethylcellulose (HPMC) 25, 100, 4000 and 15000 cPs,
xanthan gum, acacia (arabic gum),
agar-agar,
guar gum,
locust bean gum,
alginates,
molasses,
mannose and galactose polysaccharides,
chitosan,
modified starches
or mixtures thereof.

In preferred embodiments, the gelling substances are contained in the composition of the gel in amounts between 0.5% and 6%, more preferably between 1% and 4%, by weight.

Hydrophobic Gels:

Hydrophobic gels are anhydrous systems, wherein the dispersant phase is comprised of a hydrophobe dispersant.

In the preferred embodiments, the dispersant phase is selected from: vegetable oils (triglycerides), vegetable waxes, for example *Simmondsia chinensis* oil, liquid paraffin, hydrogenated polymers of 1-decene, high molecular weight silicone, for example dimethicone.

The preferred gelling agents are selected from:
colloidal silica,
fatty acid aluminum salts,
high molecular weight fatty alcohols, preferably comprised between 100 and 450 DA,
ozokerite,
vegetable waxes,
animal waxes.

Hydrophilic, Hydrophobic or Lipid Matrices:

ASA may also be formulated in special hydrophilic, hydrophobic lipid matrices or matrices that are dry, e.g. by direct compression of the drug in the polymer matrix or also mixing granules of ASA and polymer matrix before compression.

The hydrophilic matrices shall be those defined above for hydrophilic gels.

The hydrophobic matrices are preferably polyethylene, polyvinyl chloride, ethyl cellulose, acrylate polymers based, or based on the co-polymers thereof.

In these solid forms, the ASA is released thanks to the penetration of vapor or sweat into the polymer matrix. The result is a delayed and essentially constant release over time, caused by the slow dissolution and thus dispersion of the active ingredient through a network of channels existing between the compacted polymer particles.

The lipid matrices are prepared from the waxes and from the lipids. The active ingredient is released both through dispersion pores and by erosion. In certain embodiments, carnauba wax is used in combination with stearic acid.

Biodegradable matrices may also be used, as natural polymers such as proteins and polysaccharides, as such or modified, or also synthetic polymers such as aliphatic polyesters and polyanhydrides, or matrices deriving from seaweeds, such as alginic acid, may be used.

In the treatment of condylomata of the male or female genital organs, ASA will be used in creams, vaginal creams or gels or gynecological foams or vaginal suppositories for topical use.

Such pharmaceutical forms can be prepared using conventional methods and excipients well known to experts. Such methods are described, for example, in *Remington, The Science and Practice of Pharmacy*, Edited by Allen, Loyd V., Jr, 22nd edition, 2012.

Acetylsalicylic acid may also be associated with another active ingredient with inflammatory or emollient and lenitive activity, also of plant origin such as, for example *Malva sylvestris, Melaleuca alternifolia*, and *Helianthus annuus*.

In preferred embodiments, ASA is in micronized form.

In the patch or plasters according to this invention, the delayed release of the drug depends on various factors.

A first one important factor is the porosity of the matrix. For the purpose of this invention, a macro or micro-porosity matrix or also non-porous matrix may be used.

The macro-porosity matrices have pores of sizes comprised between 0.1 and 1 microns. The drug spreads through said holes.

The micro-porosity matrices have pores of sizes comprised between 50 and 200 Angstrom. In this case also the drug spreads through the pores.

In the non-porous matrices, the drug disperses through the network grid and release is slower.

Other important factors are:
the solubility of ASA, that being high enough allows its release by way of dissolution through erosion of the matrix;
the hydration/swelling ratio of the polymer matrix used,
the polymer viscosity, in that increasing the polymer's molecular weight or its viscosity in the gel layer, the dissolution of ASA slows;
the polymer concentration, in that an increase of its concentration causes an increase of the gel viscosity and therefore a slower diffusion of the drug;
the thickness of the polymer and of the hydrodynamic dispersion layer, wherein an increase of thickness causes a slower release of the drug;
the dispersion surface area, in that a smaller dispersion area accelerates the release of the drug;
the presence of diluting agents or additives, in that water-soluble diluting agents such as lactose increase the rate of release, whereas insoluble diluting agents such as dicalcium phosphate reduce the diffusion and increase erosion.

Figure 2:
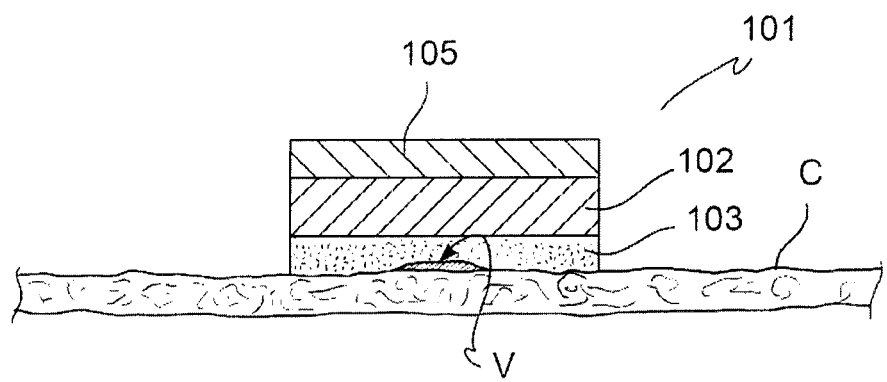
FIG. 2 depicts a schematic cross-section view of a second embodiment of the medical device according to the invention.
Figure 3:
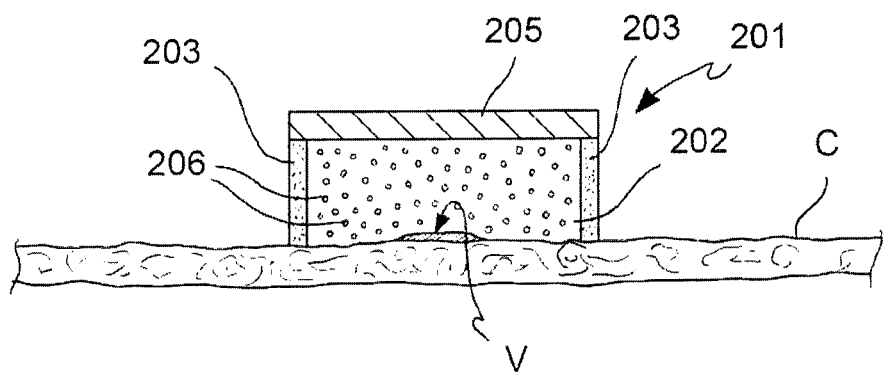
FIG. 3 depicts a schematic cross-section view of a third embodiment of the medical device according to the invention.

In FIGS. 1, 2 and 3, certain embodiments of a medical device for the topical administration are shown in accordance with this invention. In such embodiments, the polymer matrix, the outside impermeable layer and the adhesive layer are selected from those previously described.

In one embodiment, shown in FIG. 1, ASA is administered in the form of a patch or plaster 1 applied to the skin zone C on which the HPV infection to be treated, e.g. a wart V, is present.

Patch 1 comprises a solid dose 2 of ASA, e.g. a tablet, a powder, a granulate or another conventional solid form, wherein ASA may be in pure form or added with the common excipients, and an adhesive layer 3 that typically surrounds the solid dose 2.

Positioned above the solid dose 2 is a dose pusher plate 4. Patch 1 is covered on the outside with an impermeable layer 5.

In a particular preferred embodiment of patch 1 of FIG. 1, the solid dose 2 of ASA comprises ASA in a hydrophilic matrix (such as for example hydroxyethylcellulose) and/or modified starches.

In other embodiments, shown in FIG. 2, the patch or plaster 101 comprises a polymer matrix 102 containing ASA, wherein the ASA is dispersed in an adhesive polymer that is melted by solvent or hot-melted on the impermeable layer 105. The face of plaster 101 facing the surface to be treated comprises an adhesive layer 103.

In a particular preferred embodiment of patch 101 of FIG. 2, the polymer matrix 102 comprises ASA in vaseline-liquid paraffin (7:3) and urea at 20% by weight.

In other forms of the embodiment, shown in FIG. 3, the patch or plaster 201 comprises a polymer matrix 202 containing ASA in the form of microspheres, that can be obtained by suspending the ASA in an aqueous solution of a water-soluble polymer and then homogeneously dispersing such suspension in a lipophilic polymer so as to form microspheres 206 containing ASA.

The outer face of the patch 201 comprises an impermeable layer 205 while the face of the patch 201 facing the surface to be treated comprises an adhesive edge 203 surrounding the polymer matrix 202.

In a particular preferred embodiment of patch 201 of FIG. 3, the polymer matrix 202 comprises acetylsalicylic acid in sodium carboxymethylcellulose about 5% by weight, about 12% by weight ethanol, about 20% by weight glycerin, about 16% by weight propylene glycol and distilled water q.s. to 100%.

It is obvious that only certain particular embodiments of this invention have been described, to which an expert skilled in the art shall be able to make all the modifications necessary to adapt it to particular applications, without however departing from the scope of protection of this invention.

The invention claimed is:

1. A method of treating HPV skin infections consisting of administering topically to skin of a patient a therapeutically effective amount of acetylsalicylic acid,
wherein the acetylsalicylic acid is contained in a patch or plaster,
wherein the patch or the plaster consists of acetylsalicylic acid with common excipients, a layer or adhesive material facing the skin to be treated, and an impermeable layer facing outward; and,
wherein HPV skin infections in such patient are treated.

2. The method according to claim 1, wherein the HPV skin infections are of the benign type.

3. The method according to claim 2, wherein the HPV skin infections are papillomata, condylomata, condylomata of the male or female genital organs or common, plantar or flat, warts.

4. The method according to claim 1, wherein the acetylsalicylic acid is in a solid state or embedded in a polymer matrix.

5. The method according to claim 1, wherein the dosage of acetylsalicylic acid is comprised between 0.3 and 5 g/day or between 0.3 and 4 g/day, or between 0.3 and 1.2 g/day, or between 0.5 and 1 g/day.

6. The method according to claim 1, wherein the impermeable layer is selected from:
polyethylene terephthalate film (PET)
polyethylene film
polyurethane film
polyamide film
ethylene vinyl alcohol co-polymer (EVA) film
laminates comprising two or more layers of film selected from those listed above.

* * * * *